United States Patent
Quiles et al.

(10) Patent No.: US 7,881,802 B2
(45) Date of Patent: *Feb. 1, 2011

(54) TELEMETRY SWITCHOVER STATE MACHINE WITH FIRMWARE PRIORITY CONTROL

(75) Inventors: Sylvia Quiles, Edina, MN (US); Scott Vanderlinde, Plymouth, MN (US); Ken Cowan, Kirkland, WA (US); Mehdi Katoozi, Issaquah, WA (US); Krishna Sridharan, Mounds View, MN (US); Allan T. Koshiol, Lino Lakes, MN (US); Thomas J. Harris, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 696 days.

This patent is subject to a terminal disclaimer.

(21) Appl. No.: 10/914,499

(22) Filed: Aug. 9, 2004

(65) Prior Publication Data

US 2006/0030902 A1 Feb. 9, 2006

(51) Int. Cl.
*A61N 1/02* (2006.01)
(52) U.S. Cl. .......................... 607/60; 607/32
(58) Field of Classification Search .............. 607/32, 607/60; 128/903
See application file for complete search history.

(56) References Cited

U.S. PATENT DOCUMENTS

| | | | |
|---|---|---|---|
| 4,404,972 A | 9/1983 | Gordon et al. | |
| 4,519,401 A | 5/1985 | Ko et al. | |
| 4,731,814 A | 3/1988 | Becker et al. | |
| 5,292,343 A * | 3/1994 | Blanchette et al. | ............ 607/32 |
| 5,683,432 A | 11/1997 | Goedeke et al. | |
| 5,694,952 A | 12/1997 | Lidman et al. | |
| 5,752,976 A | 5/1998 | Duffin et al. | |
| 5,843,139 A | 12/1998 | Goedeke et al. | |
| 5,861,019 A | 1/1999 | Sun et al. | |
| 6,155,208 A | 12/2000 | Schell et al. | |
| 6,169,925 B1 | 1/2001 | Villaseca et al. | |
| 6,424,867 B1 * | 7/2002 | Snell et al. | .................... 607/31 |
| 6,434,429 B1 | 8/2002 | Kraus et al. | |
| 6,443,891 B1 | 9/2002 | Grevious | |
| 6,470,215 B1 | 10/2002 | Kraus et al. | |
| 6,482,154 B1 | 11/2002 | Haubrich et al. | |
| 6,490,487 B1 | 12/2002 | Kraus et al. | |
| 6,564,104 B2 | 5/2003 | Nelson et al. | |
| 6,564,105 B2 | 5/2003 | Starkweather et al. | |
| 6,574,510 B2 | 6/2003 | Von Arx et al. | |

(Continued)

FOREIGN PATENT DOCUMENTS

| | | |
|---|---|---|
| WO | WO-2005/099817 A1 | 10/2005 |
| WO | WO-2006/020546 A1 | 2/2006 |
| WO | WO-2006/020549 A1 | 2/2006 |

OTHER PUBLICATIONS

Quiles, Sylvia, "Automatic Power Control for a Radio Frequency Transceiver of an Implantable Device", U.S. Appl. No. 10/914,496, filed Aug. 9, 2004, 23 pgs.

Seeberger, M., "Dynamic Telemetry Link Selection for an Implantable Device", U.S. Appl. No. 10/914,638, filed Aug. 9, 2004, 35 pgs.

"International Search Report and Written Opinion for Application No. PCT/US2005/028059, mailed Dec. 1, 2005.", 13 pgs.

(Continued)

*Primary Examiner*—Scott M Getzow
*Assistant Examiner*—Joseph M Dietrich
(74) *Attorney, Agent, or Firm*—Schwegman, Lundberg & Woessner, P.A.

(57) ABSTRACT

The selection of one communication channel from a plurality of available channels is determined by a state machine. In an automatic selection mode, a first telemetry system has priority over other telemetry systems. A communication session is in progress based on session initiation and termination triggers. An override function allows manual selection of a telemetry system.

25 Claims, 5 Drawing Sheets

U.S. PATENT DOCUMENTS

| | | | |
|---|---|---|---|
| 6,585,644 | B2 | 7/2003 | Lebel et al. |
| 6,600,952 | B1 | 7/2003 | Snell et al. |
| 6,622,050 | B2 | 9/2003 | Thompson |
| 6,687,546 | B2 | 2/2004 | Lebel et al. |
| 6,993,393 | B2 | 1/2006 | Von Arx et al. |
| 7,027,872 | B2 | 4/2006 | Thompson |
| 7,406,349 | B2 | 7/2008 | Seeberger et al. |
| 7,539,541 | B2 * | 5/2009 | Quiles et al. .................. 607/31 |
| 7,738,964 | B2 | 6/2010 | Von Arx et al. |
| 2003/0083719 | A1 | 5/2003 | Shankar et al. |
| 2003/0114897 | A1 * | 6/2003 | Von Arx et al. ............... 607/60 |
| 2003/0114898 | A1 | 6/2003 | Von Arx et al. |
| 2003/0149459 | A1 | 8/2003 | Von Arx et al. |
| 2004/0030260 | A1 | 2/2004 | Von Arx |
| 2005/0204134 | A1 | 9/2005 | Von Arx et al. |
| 2005/0240245 | A1 | 10/2005 | Bange et al. |
| 2005/0283208 | A1 | 12/2005 | Von Arx et al. |
| 2006/0030901 | A1 | 2/2006 | Quiles et al. |
| 2006/0030903 | A1 | 2/2006 | Seeberger et al. |
| 2006/0116744 | A1 | 6/2006 | Von Arx et al. |
| 2008/0262573 | A1 | 10/2008 | Seeberger et al. |
| 2010/0152816 | A1 | 6/2010 | Von Arx et al. |

OTHER PUBLICATIONS

"U.S. Appl. No. 10/025,223, Prosecution File History", 30 pgs.
"U.S. Appl. No. 10/025,223, Prosecution File History", 55 pgs.
"U.S. Appl. No. 10/914,638, Prosecution File History", 41 pgs.
"International Application No. PCT/US2005/028052 International Preliminary Report on Patentability mailed Feb. 22, 2007", 8 pgs.
"International Application No. PCT/US2005/028052 International Search Report and Written Opinion mailed Nov. 29, 2005", 12 pgs.
"International Application No. PCT/US2005/028059 International Preliminary Report on Patentability mailed Feb. 13, 2007", 9 pgs.
"International Application No. PCT/US2005/028059 International Search Report and Written Opinion mailed Jan. 12, 2005", 13 pgs.
"U.S. Appl. No. 10/914,496 Non-Final Office Action mailed Mar. 18 2008", 9 pgs.
"U.S. Appl. No. 10/914,638, Notice of Allowance mailed Oct. 22, 2007", 4 pgs.
"U.S. Appl. No. 10/914,638 Notice of Allowance mailed Mar. 21, 2008", 4 pgs.
"Prosecution File History for U.S. Appl. No. 10/025,223", 55 pgs.
"U.S. Appl. No. 11/325,584 Non-Final Office Action mailed Apr. 10, 2008", 6 pgs.
"Part III—Department of Health and Human Services, Office of the Secretary—45 CFR Part 142—Security and Electronic Signature Standards; Proposed Rule", *Federal Register*, 63(155) (Aug. 12, 1998), 43241-43280.
"Public Law 104-191 [H.R. 3103]—Health Insurance Portability and Accountability Act of 1996", *United States Public Laws—104th Congress—2nd Session*, (Aug. 21, 1996), 78 pgs.
Diffie, W., "The First Ten Years of Public-Key Cryptography", *Proceedings of the IEEE*, 76(5), (May 1988), 560-577.
Hammond, E., "Perspectives on Implementation of Administrative Simplification Provisions of P.L. 104-191", *National Committee on Vital and Health Statistics, Subcommittee on Health Data Needs, Standards and Security*, (Feb. 11, 1997), 4 pgs.
"U.S. Appl. No. 10/914,496, Final Office Action mailed Sep. 22, 2008", 12 pgs.
"U.S. Appl. No. 10/914,496, Notice of Allowance mailed Jan. 16, 2009", 4 pgs.
"U.S. Appl. No. 10/914,496, Response filed Nov. 24, 2008 to Final Office Action mailed Sep. 22, 2008", 9 pages.
"U.S. Appl. No. 11/325,584, Response filed Jul. 10, 2008 to Non Final Office Action mailed Apr. 10, 2008", 9 pgs.
"U.S. Appl. No. 11/325,584 Final Office Action mailed Oct. 24, 2008.", 5 pgs.
"U.S. Appl. No. 12/145,343, Restriction Requirement mailed Aug. 26, 2010", 7 pgs.
"European Application No. 05783882.3, Response filed Oct. 22, 2009 to Communication mailed Jun. 16, 2009", 7 pgs.

* cited by examiner

TELEMETRY SWITCHOVER STATE MACHINE WITH FIRMWARE PRIORITY CONTROL

CROSS-REFERENCE TO RELATED DOCUMENTS

This document is related to U.S. patent application Ser. No. 10/914,496, entitled "AUTOMATIC POWER CONTROL FOR A RADIO FREQUENCY TRANSCEIVER OF AN IMPLANTABLE DEVICE," filed Aug. 9, 2004 by Quiles et al. and is incorporated herein by reference.

This document is related to U.S. patent application Ser. No. 10/914,638, entitled "DYNAMIC TELEMETRY LINK SELECTION FOR AN IMPLANTABLE DEVICE," filed Aug. 9, 2004 by Seeberger et al. and is incorporated herein by reference.

This document is related to U.S. patent application Ser. No. 10/025,223, entitled "A TELEMETRY DUTY CYCLE MANAGEMENT SYSTEM FOR AN IMPLANTABLE MEDICAL DEVICE," filed Dec. 19, 2001 by Von Arx et al. and is incorporated herein by reference.

TECHNICAL FIELD

This document pertains generally to implantable devices, and more particularly, but not by way of limitation, to a telemetry switchover state machine with firmware priority control.

BACKGROUND

Telemetry between an implantable medical device and an external device has traditionally required the use of an inductive wand. Physicians and patients often find this inconvenient and unacceptable because of the limited communication range and limited bandwidth.

Some implantable devices are equipped with a radio frequency telemetry system having greater range and higher bandwidth. However, the increased current drain associated with radio frequency telemetry reduces the device longevity.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed herein.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The examples may be combined, other examples may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Introduction

In one example, an implantable device includes a first telemetry circuit and a second telemetry circuit as well as circuitry and programming to automatically switch between the two telemetry circuits. The two telemetry circuits differ in terms of bandwidth, reliability, power consumption or other factors.

The implantable device functions as a slave relative to the external device which functions as a master. The external device selects one of a plurality of telemetry links to use in communicating with the implantable device. In one example, the implantable device remains continuously receptive to communicating using an inductive link.

An example of the present system entails two concurrently operating state machines that are tied together. Each state machine enables communication via a particular telemetry link. In one example, priority lies with a first telemetry link in that valid communications received through the first telemetry link enjoy priority over a second telemetry link. In one example, priority lies with an inductive telemetry link.

Structure

Figure 1:
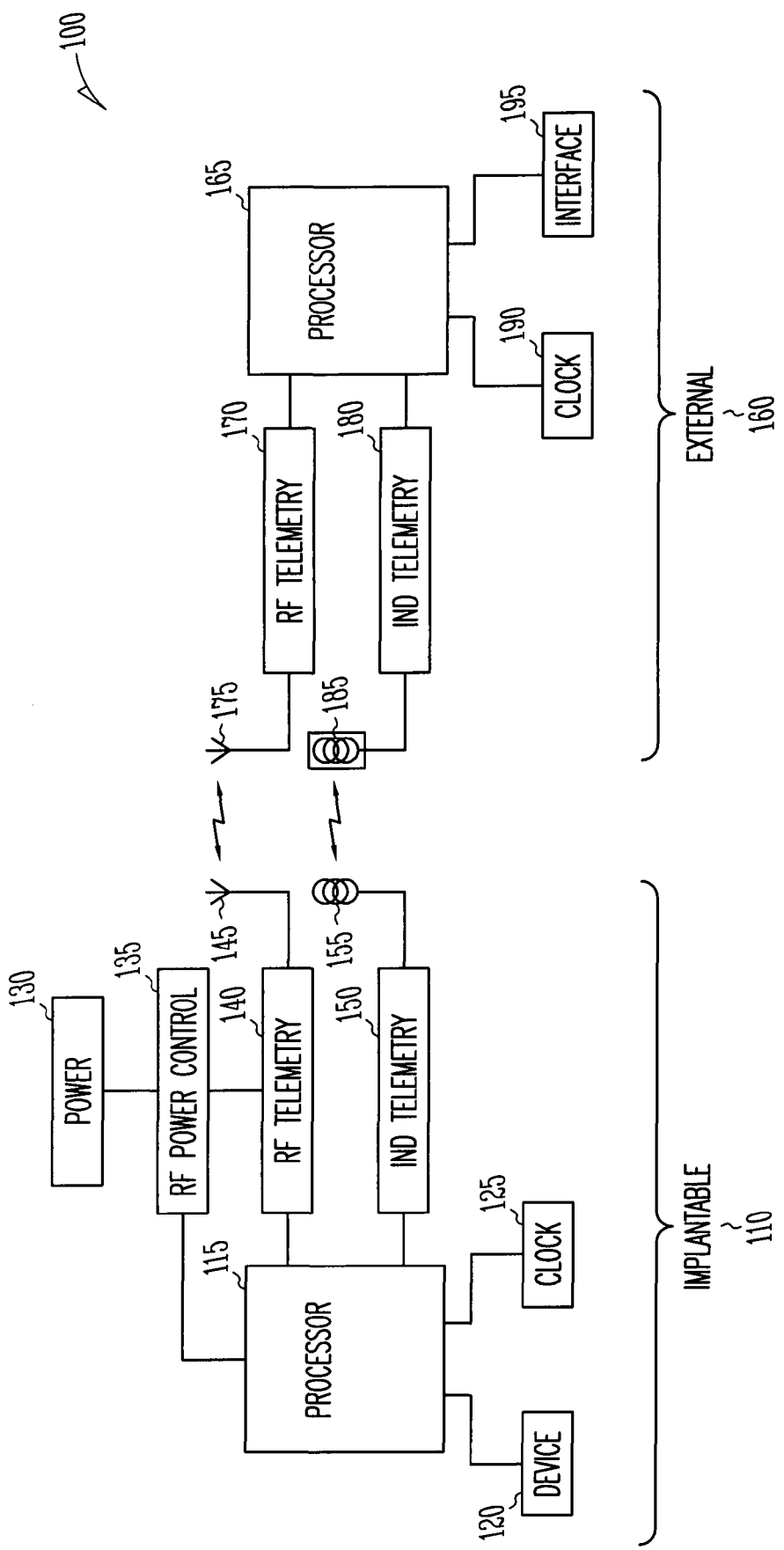
FIG. 1 includes an illustration of an implantable device in communication with an external device.

FIG. 1 illustrates system 100 including implantable device 110 and external device 160, each having dual telemetry circuits.

Implantable device 110 includes processor 115 coupled to device 120. Device 120, in various examples, includes a pulse generator (such as a pacemaker, a cardiac rhythm therapy device, a heart failure or cardiac resynchronization device, a cardioverter/defibrillator, a pacer/defibrillator), a drug delivery device (such as an implantable drug pump) and a monitor circuit. In addition, processor 115 is coupled to a far field telemetry circuit, radio frequency telemetry circuit 140 and a near field telemetry circuit, inductive telemetry circuit 150. Radio frequency telemetry circuit 140 includes a transmitter circuit and a receiver circuit (also referred to as a transceiver circuit) coupled to radio frequency antenna 145. Antenna 145 is configured to generate and receive far field signals. As used herein, the phrase radio frequency refers to far field communications conducted using far field radiation and reception where the field distribution is essentially independent of distance from the source. Power 130 is delivered to radio frequency telemetry circuit 140 by power control 135 and in one example, includes a battery. Power control 135 operates on instructions received from processor 115. Both the far field telemetry circuit and the near field telemetry circuit are configured to enable wireless data telemetry with an external device.

Inductive telemetry circuit 150 is coupled to inductive antenna 155. In one example, inductive telemetry circuit 150 includes a continuously powered transceiver. Antenna 155 is configured for near field transmission and reception, and, in one example, includes a loop antenna. Near field refers to radiation and reception where the field distribution is a function of distance from the source.

Implantable device 110 includes clock 125 coupled to processor 115. Clock 125 provides a timing signal for the benefit of processor 115.

External device 160 includes processor 165 coupled to interface 195. Interface 195, in various examples, includes a display monitor, a printer, a keyboard, a touch-sensitive screen, a cursor control, a speaker, a microphone, a storage device and a network interface device. External device 160, in one example, includes a programmer for use by a physician or other medical personnel at the time of implantation as well as during follow-up visits. As a programmer, external device 160 allows interrogation as well as programming of implantable device 110, and accordingly, includes a user-accessible interface. External device 160, in one example, includes a remote interrogation device (sometimes referred to as a repeater) which allows connecting with a bi-directional communication network such as a local area network (Ethernet), a wide area network (such as the Internet) or telephone lines in a home (plain old telephone service via the public switched telephone network). In addition, processor 165 is coupled to radio frequency telemetry circuit 170 and inductive telemetry circuit 180. Radio frequency telemetry circuit 170 includes a transceiver coupled to radio frequency antenna 175. Antenna 175, like antenna 145, is configured to generate and receive far field signals.

Inductive telemetry circuit 180 includes a transceiver circuit coupled to inductive antenna 185. Antenna 185, in one example, is part of a hand-operable device sometimes referred to as a wand. The wand enables inductive communications over a short range. In one example, the inductive communication range is approximately 6 inches. Antenna 185, like antenna 155, is configured to generate and receive near field signals and, in one example, includes a loop antenna.

External device 160 includes clock 190 coupled to processor 165. Clock 190 provides a timing signal for the benefit of processor 165.

State Diagrams

Figure 2:
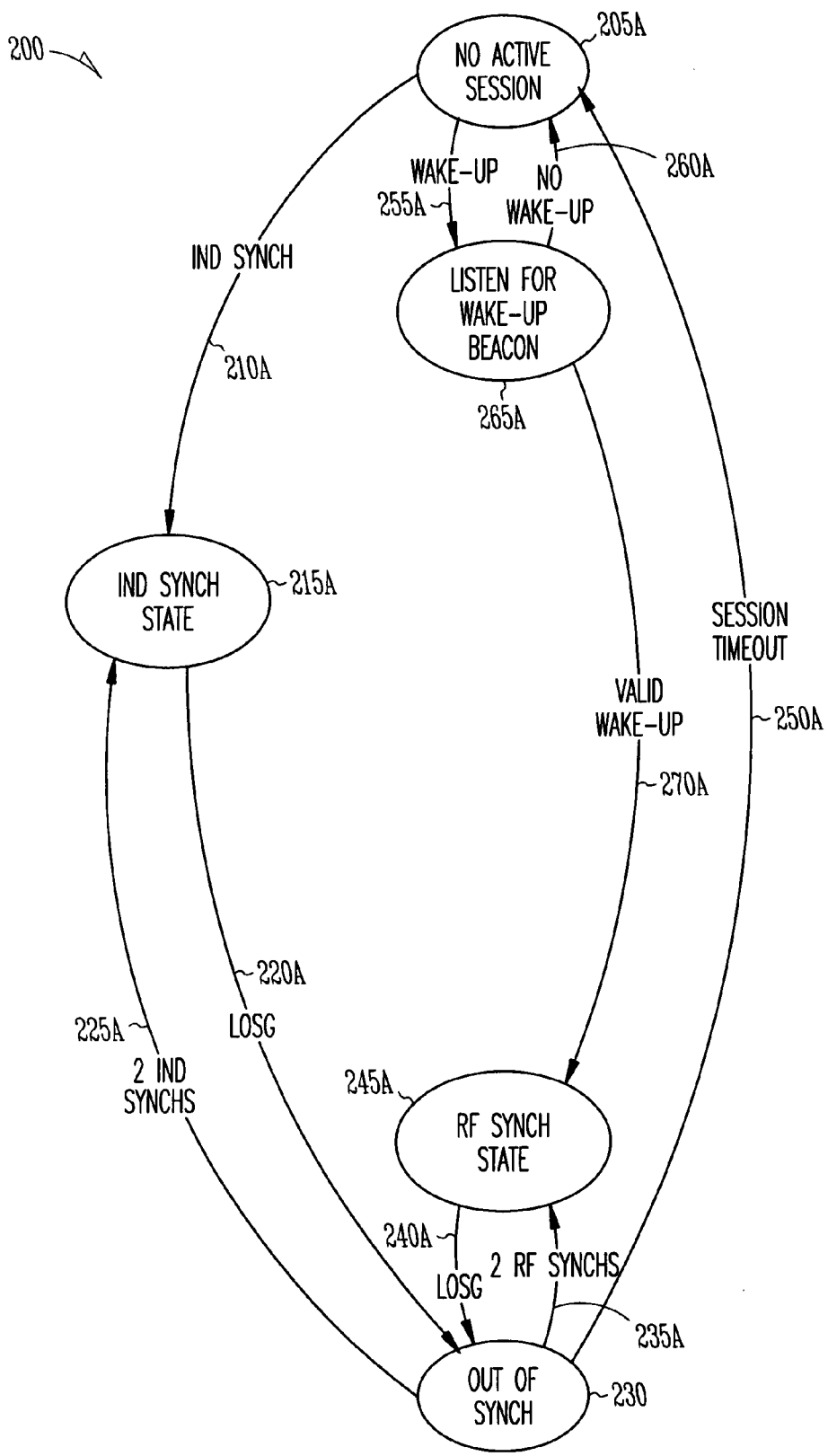
FIGS. 2, 3 and 4 include illustrations of state diagrams.

In one example, system 100 operates according to state diagram 200 as shown in FIG. 2. State diagram 200 illustrates an example of communication session initiation, automatic session termination and simultaneous monitoring using a system including a dual telemetry implantable device.

At state 205A, state diagram 200 shows an initial condition at a time where implantable device 110 is not actively engaged in a communication session with external device 160. Accordingly, no radio frequency or inductive telemetry link has been established.

An inductive communication session is established by proceeding along path 210A to inductive synchronization state 215A. Inductive telemetry circuit 180 of external device 160 transmits a sequence of synchronization signals generated by processor 165. In one example, the sequence of synchronization signals are communicated by a wand (including inductive antenna 185) positioned near inductive antenna 155. In one example, the sequence includes two inductive synchronization signals, however, other signals are also contemplated.

Upon detecting the inductive synchronization signals, implantable device 110 enters inductive synchronization state 215A during which implantable device 110 and external device 160 engage in an exchange of data or signals using inductive telemetry.

Upon receiving a signal, implantable device 110 exits inductive synchronization state 215A and transitions to out of synchronization state 230 via path 220A. Label LOSG, as it appears on path 220A, denotes the loss of the synchronization signal. In one example, external device 160 transmits a signal to request that implantable device 110 exit inductive state 215A. In one example, implantable device 110 exits inductive synchronization state 215A upon detecting the loss of the synchronization signal for a predetermined period of time in excess of a particular value.

In state 230, implantable device 110 monitors for both an inductive synchronization signal and a radio frequency synchronization signal, each of which represent departure routes from state 230. Thus, implantable device 110 can exit state 230 by receiving two inductive synchronization signals (path 225A), receiving two radio frequency synchronization signals (path 235A) and also upon session time-out (path 250A). From state 230, if implantable device 110 receives two inductive synchronization signals, as shown by path 225A, then implantable device 110 returns to state 215A. If implantable device 110 receives two radio frequency synchronization signals, as shown by path 235A, then implantable device 110 transitions to radio frequency synchronization state 245A. If implantable device 110 does not receive a synchronization signal (either inductive or radio frequency) for a predetermined period of time, then, as shown by path 250A, implantable device 110 treats this as a session time-out and returns to state 205A where no communication session is active. In one example, the predetermined period of time for a session time-out is 1 hour. Following the session time-out period (as determined by processor 115 based on data provided by clock 125), radio frequency telemetry circuit 140 is powered down by radio frequency power control 135 on an instruction received from processor 115. Implantable device 110 may not receive the synchronization signal because, for example, the external device 160 has stopped transmitting.

While in state 245A, implantable device 110 and external device 160 engage in an exchange of data or signals using radio frequency telemetry. If, while in state 245A, implantable device 110 loses the radio frequency synchronization signal for a period of time in excess of a particular value, then, as shown by path 240A, implantable device 110 drops out of state 245A and returns to out of synchronization state 230.

From state 205A, implantable device 110 periodically wakes up, as shown at path 255A, transitions to state 265A and monitors for a predetermined wake-up beacon. If no wake-up beacon is received within a predetermined period of time, then, as shown by path 260A, implantable device 110 returns to state 205A where no session is active. If implantable device 110 receives a valid wake-up beacon, as shown by path 270A, then implantable device 110 transitions to radio frequency synchronization state 245A. In one example, a wake-up beacon is transmitted from a remote interrogation device using radio frequency telemetry circuit 170.

Figure 3:
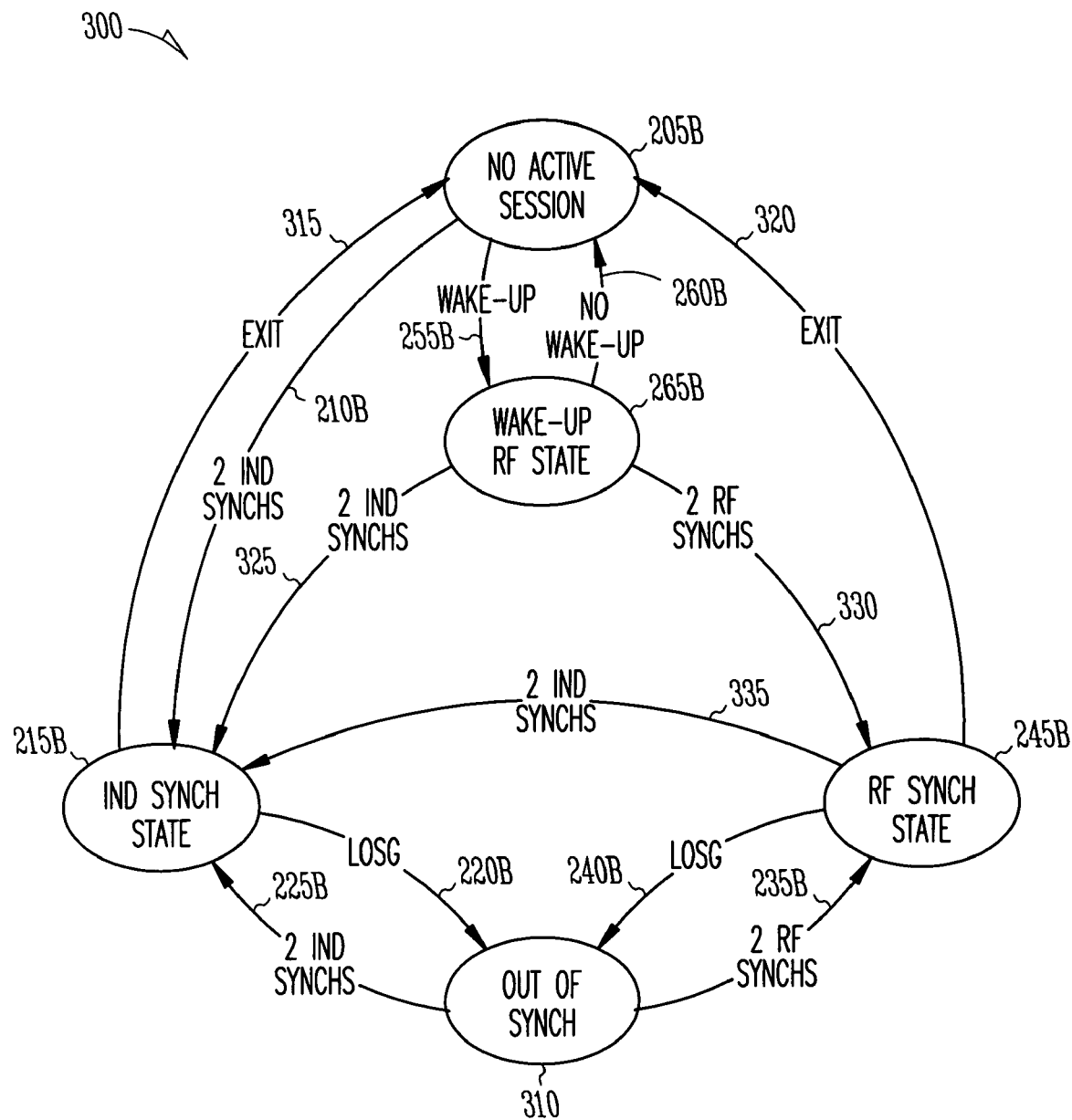

In one example, system 100 operates according to state diagram 300 as shown in FIG. 3. State diagram 300 illustrates an example where, by default, a communication session operates using an inductive telemetry circuit unless a particular signal is received to communicate using a radio frequency telemetry circuit. In addition, state diagram 300 illustrates an example of automatic link switching with inductive telemetry priority as well as externally controlled session termination.

At state 205B, state diagram 300 shows an initial condition where implantable device 110 is not actively engaged in a communication session with external device 160. Accordingly, no radio frequency or inductive telemetry link has been established.

An inductive communication session is established by proceeding along path 210B to inductive synchronization state 215B. Inductive telemetry circuit 180 of external device 160 transmits a sequence of synchronization signals generated by processor 165. In one example, the sequence of synchronization signals are communicated by a wand (including inductive antenna 185) positioned near inductive antenna 155. In one example, the sequence includes two inductive synchronization signal, however, other signals are also contemplated.

Upon detecting the inductive synchronization signals, implantable device 110 enters inductive synchronization state 215B during which implantable device 110 and external device 160 engage in an exchange of data or signals using inductive telemetry.

Upon receiving a signal, implantable device 110 exits inductive synchronization state 215B and transitions to out of synchronization state 310 via path 220B. In one example, external device 160 transmits a signal to request that implantable device 110 exit inductive state 215B. In one example, implantable device 110 exits inductive synchronization state 215B upon detecting the loss of the synchronization signal for a predetermined period of time in excess of a particular value. A physician may cause implantable device 110 to exit inductive synchronization state 215B by removing the inductive wand or otherwise terminating the communication session. From inductive synchronization state 215B, the communication session can be terminated, as shown by path 315 and implantable device 110 then returns to state 205B where the communication session is inactive.

In state 310, implantable device 110 monitors for both an inductive synchronization signal and a radio frequency synchronization signal, each of which represent departure routes from state 310. Thus, implantable device 110 can exit state 310 by receiving two inductive synchronization signals (path 225B), receiving two radio frequency synchronization signals (path 235B). From state 310, if implantable device 110 receives two inductive synchronization signals, as shown by path 225B, then implantable device 110 returns to state 215B. If implantable device 110 receives two radio frequency synchronization signals, as shown by path 235B, then implantable device 110 transitions to radio frequency synchronization state 245B. If implantable device 110 does not receive a synchronization signal (either inductive or radio frequency) for a predetermined period of time, then, implantable device 110 treats this as a session time-out and returns to state 205B where no communication session is active. In one example, the predetermined period of time for a session time-out is 1 hour. Following the session time-out period (as determined by processor 115 based on data provided by clock 125), radio frequency telemetry circuit 140 is powered down by radio frequency power control 135 on an instruction received from processor 115. Implantable device 110 may not receive the synchronization signal because, for example, the external device 160 has stopped transmitting.

While in state 245B, implantable device 110 and external device 160 engage in an exchange of data or signals using radio frequency telemetry. If, while in state 245B, implantable device 110 loses the radio frequency synchronization signal for a period of time in excess of a particular value, then, as shown by path 240B, implantable device 110 drops out of state 245B and returns to out of synchronization state 310. A physician may cause implantable device 110 to exit state 245B by terminating the communication session.

From state 205B, implantable device 110 periodically wakes up, as shown at path 255B, transitions to state 265B and monitors for a predetermined wake-up beacon. If no wake-up beacon is received within a predetermined period of time, then, as shown by path 260B, implantable device 110 returns to state 205B where no session is active. If implantable device 110 receives an inductive synchronization signal, as shown by path 325, or a radio frequency synchronization signal, as shown by path 330, then implantable device 110 transitions to inductive synchronization state 215B or radio frequency synchronization state 245B, respectively. In one example, a wake-up beacon is transmitted from a remote interrogation device using radio frequency telemetry circuit 170.

In state 245B, implantable device 110 and external device 160 engage in a periodic exchange of data or signals using radio frequency telemetry. Departure routes from state 245B include loss of radio frequency synchronization signal (path 240B), receipt of two inductive synchronization signals (path 335) or receipt of a termination signal (path 320).

If, while in state 245B, implantable device 110 receives two inductive synchronization signals, as shown by path 335, then implantable device 110 returns to inductive synchronization state 215B. If, while in state 245B, implantable device 110 receives a communication session termination signal, as shown by path 320, then implantable device 110 returns to state 205B where no session is active.

In one example, implantable device 110 can proceed to radio frequency synchronization state 245B without first transitioning through an inductive communication state. A remote interrogation device, or other device adapted for connecting with a telephone outlet or other communication network interface, includes radio frequency telemetry circuit 170 but may not have an inductive wand. Implantable device 110 periodically wakes up at one minute intervals, as shown by path 255B, and, at state 265B, listens for a synchronization signal. If a synchronization signal is not received while at state 265B, then implantable device 110 returns to no active session state 205B via path 260B. Depending upon the type of synchronization signal received during the wake-up period of the duty cycle, implantable device 110 will transition to either inductive synchronization state 215B (using path 325) or radio frequency synchronization state 245B (using path 330).

When in state 215B, implantable device 110 is receptive, and responsive, to only an inductive synchronization signal. When in either state 310 or state 245B, implantable device 110 is receptive, and responsive, to both an inductive synchronization signal and a radio frequency synchronization signal. As to state 245B, implantable device 110 will continue to communicate using radio frequency telemetry circuit 140 until an inductive synchronization signal is received, at which time, implantable device 110 will switch to inductive synchronization state 215B. The non-responsiveness of implantable device 110 to a radio frequency synchronization signal when in state 215B is a manifestation of the selection of inductive link priority.

According to one example, if implantable device 110 drops the synchronization signal for a period of 100 milliseconds, then implantable device 110 will exit from inductive synchronization state 215B and transition to out of synchronization state 310. If, while in state 310, implantable device 110 receives two radio frequency synchronization signals, then implantable device 110 transitions to radio frequency synchronization state 245B.

In one example, the radio frequency link is given priority. In one example, implantable device 110 is receptive, and responsive, to a radio frequency synchronization signal when in state 215B. For example, upon receiving a radio frequency synchronization signal while in state 215B, implantable device 110 transitions to radio frequency synchronization state 245B.

Figure 4:
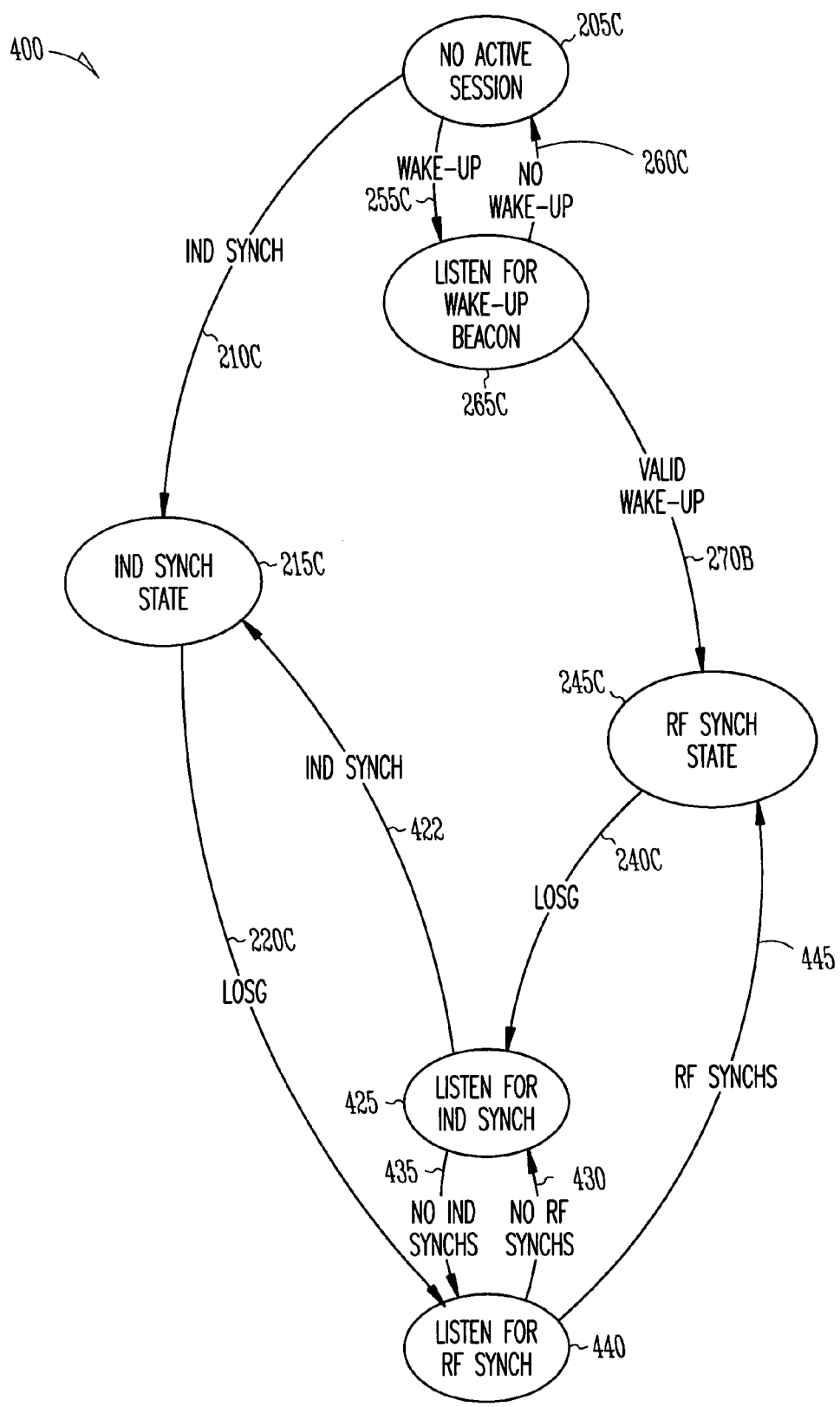

In one example, system 100 operates according to state diagram 400 as shown in FIG. 4. State diagram 400 illustrates an example in which multiple telemetry links are monitored in a sequential manner when not in a synchronized state. Monitoring in a sequential manner entails alternately monitoring on one telemetry link or another in a serial order during a time when synchronization on an active communication link is lost. As noted earlier, state diagrams 200 and 300 illustrate examples of concurrent or simultaneous monitoring of multiple telemetry links.

State diagram 400 illustrates an initial condition at state 205C where implantable device 110 is not actively engaged in a communication session with external device 160. Accordingly, no radio frequency or inductive telemetry link has been established.

An inductive communication session is established by proceeding along path 210C to inductive synchronization state 215C. Inductive telemetry circuit 180 transmits a sequence of synchronization signals generated by processor 165. In one example, the sequence of synchronization signals are communicated by a wand (including inductive antenna 185) positioned near inductive antenna 155. In one example, the sequence includes two inductive synchronization signals, however, other signals are also contemplated.

Upon detecting the inductive synchronization signals, implantable device 110 enters inductive synchronization state 215C during which implantable device 110 and external device 160 engage in an exchange of data or signals using inductive telemetry.

Upon receiving a signal, implantable device 110 exits inductive synchronization state 215C and transitions to listen for radio frequency synchronization state 440 via path 220C. In one example, external device 160 transmits a signal to request that implantable device 110 exit inductive state 215C. In one example, implantable device 110 exits inductive synchronization state 215C upon detecting the loss of the synchronization signal for a predetermined period of time in excess of a particular value. A physician may cause implantable device 110 to exit inductive synchronization state 215C by removing the inductive wand or otherwise terminating the communication session.

In state 440, implantable device 110 listens for a radio frequency synchronization signal, the presence or absence of which represents departure routes from state 440. Thus, implantable device 110 can exit state 440 by detecting two radio frequency synchronization signals (path 445). In addition, if the radio frequency synchronization signals are not received (path 430) in a predetermined period of time, then implantable device 110 transitions to state 425 during which implantable device 110 listens for an inductive synchronization signal.

Departure routes from state 440 include implantable device 110 not receiving a radio frequency synchronization signal (path 430) and implantable device 110 receiving a radio frequency synchronization signal (path 445). If implantable device 110 does not receive a radio frequency synchronization signal, after a predetermined time, as shown by path 430, then implantable device 110 transitions to state 425 where implantable device 110 listens for an inductive synchronization signal.

While in state 425, implantable device 110 monitors for an inductive synchronization signal. If, while in state 425, implantable device 110 does not receive an inductive synchronization signal within a predetermined time period, then, as shown by path 435, implantable device 110 returns to state 440. If, while in state 425, implantable device 110 detects an inductive synchronization signal, then, as shown by link 422, implantable device 110 transitions to inductive synchronization state 215C.

If, while in state 440, implantable device 110 receives a radio frequency synchronization signal, as shown by path 445, then implantable device 110 transitions to radio frequency synchronization state 245C. While in radio frequency synchronization state 245C, if implantable device 110 loses the radio frequency synchronization signal for a time in excess of a predetermined time period, as shown by path 240C, then implantable device 110 returns to state 425 and listens for an inductive synchronization signal.

From state 205C, implantable device 110 periodically wakes up, as shown by path 255C, transitions to state 265C and listens for a predetermined wake-up beacon. If a valid wake-up beacon is not received within a predetermined period of time, then, as shown by path 260C, implantable device 110 returns to state 205C where no session is active. If, while in wake-up state 265C, implantable device 110 receives a valid wake-up signal, as shown by path 270B, then implantable device 110 reverts to radio frequency synchronization state 245C.

Figure 5:
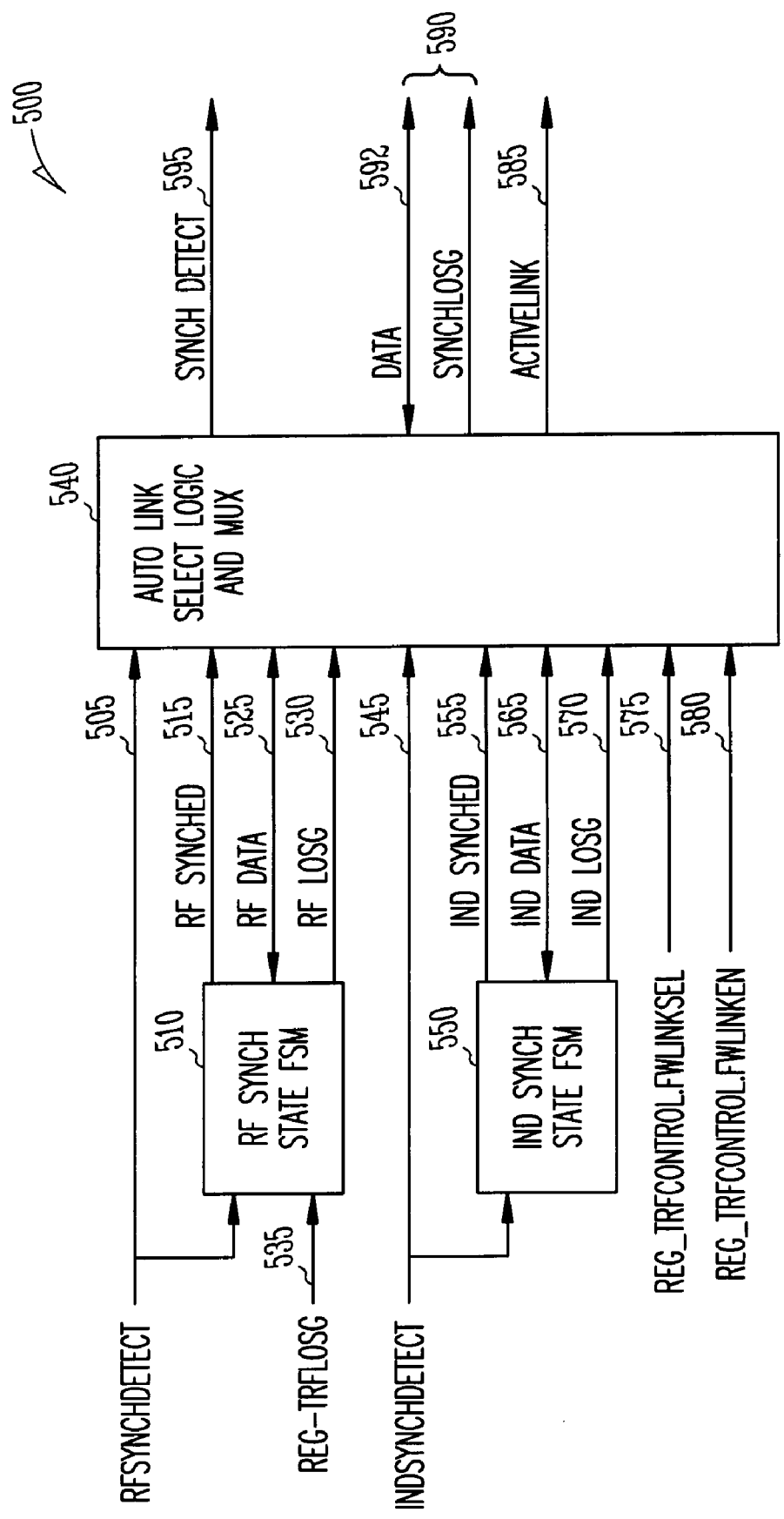
FIG. 5 includes an illustration of a block diagram for a portion of an implantable device.

FIG. 5 illustrates block diagram 500 corresponding to a portion of implantable device 110. Radio frequency synchronization state machine 510 and inductive synchronization state machine 550 operate independently and are each coupled to block 540. In various examples, state machines 510 and 550 are implemented in circuitry, logical gates and a processor executing an algorithm stored in a memory. Block 540 includes automatic link selection logic as well as a multiplexer. FIG. 5 illustrates how state machine 510 and state machine 550 are fed into a set of common communication lines 590. Block 540 includes logic and circuitry to select between lines 515, 525 and 530 and lines 555, 565 and 570.

In diagram 500, block 540 is actively programmable using select line 575 and enable line 580. A microprocessor coupled to select line 575 and enable line 580 allow the circuit of diagram 500 to operate in an automatic mode, an inductive mode or a radio frequency mode. Line 580 is an enable line which determines if the signal specified using select line 575 is to be activated or not. For example, if line 580 is enabled (logical value of 1), then the value specified by select line 575 is controlling. In one example, line 575 is set to a logical value of "0" for inductive and a logical value of "1" for radio frequency communication. If enable line 580 is not enabled (logical value of "0"), then either state machine 510 or state machine 550 is selected based on the logic and firmware encoded in block 540. Both state machine 510 and state machine 550 are used for both receiving and transmitting.

In one example, external device 160 selects a single telemetry link for communicating. The circuitry illustrated in FIG. 5 allows implantable device 110 to select the appropriate telemetry link corresponding to that used by external device 160. When external device 160 stops and restarts on either one or the other of the telemetry links, then the circuitry of FIG. 5 selects the telemetry link for implantable device 110.

When line 580 is not enabled, the circuitry of FIG. 5 selects the telemetry link for implantable device 110 based on an instruction received from external device 160. In other words, if external device 160 is synchronizing with implantable device 110 using a radio frequency telemetry link, then radio frequency synchronization state machine 510 will be active and inductive synchronization state machine 550 will be inactive and data appearing on line 592 will be radio frequency telemetry data.

Line 515 indicate that radio frequency telemetry circuit 140 is in the radio frequency synchronization state. Line 555 indicate that inductive telemetry circuit 150 is in the inductive synchronization state. Line 505 indicates that a radio frequency synchronization signal has been received and line 545 indicates that an inductive synchronization signal has been received. Line 535 indicates the programmed value for the radio frequency loss of signal line. Line 595 is a status signal to processor 115 which indicates when either the radio frequency state machine or the inductive state machine are in their synchronization state.

Radio frequency data lines 525 and inductive data lines 565 are bidirectional data lines. Depending on the logic levels present on select line 575 and enable line 580, either radio frequency or inductive data will be present on bidirectional data line 592.

Active link 585 reflects the active telemetry link and, in one example, is at a logic level of "0" to indicate inductive telemetry is currently active and at a logic level of "1" to indicate radio frequency telemetry is currently active.

In one example, either external device 160 or implantable device 110 is sending data. During a communication session, external device 160 periodically transmits a synchronization, or timing, pulse upon which implantable device 110 synchronizes. In the absence of the synchronization pulse, the communication session is inactive.

In one example, the communication link is referred to as half-duplex meaning that only one device can be transmitting at a time.

When implantable device 110 is sending data back to external device 160, it sends a synchronization pulse interspersed with continuous, real-time data from implantable device 110.

External device 160 can send data, commands or instruction to implantable device 110 and also receive responses from implantable device 110. While a session is active, if external device 160 is not sending commands or instructions to implantable device 110, then implantable device 110 is sending internal electrocardiograms and other data from the heart. At a time when external device 160 is not sending commands or instructions, external device 160 is sending out timing pulses and implantable device 110 continues to send data which is displayed or otherwise processed using external device 160.

During a communication session, external device 160 periodically sends a timing signal upon which implantable device 110 synchronizes data transmissions. Implantable device 110 continuous to send data while in the synchronized mode. External device 160 receives the continuous stream of data from implantable device 110 and generates a real-time visual display, stores in memory or otherwise processes the data. In order to transmit to implantable device 110, external device 160 briefly interrupts the sequence of timing pulses. Implantable device 110, upon detecting that two synchronization pulses are missing, suspends data transmissions and reverts to a receive mode using the active communication link. In the receive mode, implantable device 110 is receptive to incoming commands, instructions or data from external device 160. In addition, implantable device 110 continues to use the most recent state machine and awaits an indication as to whether the telemetry selection signal has been lost.

In one example, the time period for the loss of synchronization is less than the time period for the loss of signal used to transition from one state machine to another. In one example, the time period for the loss of signal is 100 milliseconds and the time period for the loss of synchronization is 20 milliseconds, however periods of other duration are also contemplated. In one example, the time period for terminating a communication session is greater than the time period for the loss of signal.

In one example, implantable device 110 is configured to communicate in either an inductive mode, a radio frequency mode or an automatic mode. External device 160 selects the telemetry communication mode using a hardware switch or firmware selection. Both the starting point and ending point of a communication session are marked by triggers from external device 160. Based on the starting point trigger, or other factor, the implantable device transitions from an inactive mode into one of three communication modes. In automatic mode, other factors determine which link to use for communicating. Those factors can include, for example, signal to noise ratio, bandwidth requirements as well as the identity of the communication link used to initiate the communication session.

Exemplary Alternatives

In one example the signal used to transition from one telemetry link to another telemetry link includes a pair of synchronization signals sent from external device 160. In one example, more or less than two synchronization signals are used to trigger the transition from one telemetry link to another telemetry link.

In one example, an instruction, flag or other coded signal is sent by external device 160 to command implantable device 110 to transition from one telemetry link to another telemetry link.

In one example, implantable device 110 waits for a programmable period of time before determining if a synchronization signal has been lost. The period of time can be programmed by an instruction received from external device 160. In one example, the duration of the loss of signal trigger is determined by a value in a memory register or determined through a programmable control. In one example, if a synchronization signal is not received within a predetermined period of time while monitoring for signal using a first telemetry circuit, then the implantable device will revert to a second telemetry circuit. The timing signal, derived from clock 125, determines when the signal has been lost and provides the triggering event to toggle to a different telemetry circuit. The duration of the predetermined period is programmable.

In one example, implantable device 110 waits for a programmable period of time before determining that the communication session has timed out. The period of time can be programmed by an instruction received from external device 160.

In one example, telemetry circuits in addition to, or in lieu of, inductive telemetry and radio frequency telemetry, are contemplated. For example, more than one inductive or radio frequency antenna may be connected to a particular telemetry circuit. In addition, implantable device 110 can include more than one radio frequency telemetry circuit, each of which operate using a different carrier frequency or communication protocol. In various examples, different communication channels are used, including an optical channel, an ultrasonic channel and an acoustical channel. In one example, a radio frequency telemetry circuit enjoys priority over a second telemetry circuit as well as a third telemetry circuit.

In one example, inductive telemetry circuit 150 has static priority over radio frequency telemetry circuit 140. Other arrangements for priority of the telemetry circuits are also contemplated. In one example with an implantable device having three telemetry systems or circuits, a selected telemetry circuit enjoys priority and any valid signal received using the selected telemetry circuit will be given priority over other signals received using the other telemetry circuits. If the selected telemetry circuit is unavailable, then a second telemetry circuit is used and as between signals received using both the second telemetry circuit and a third telemetry, that received by the second telemetry circuit enjoys priority.

In one example, a dynamic priority system is established wherein the priority as between multiple telemetry circuits is determined based on one or more selection factors. For example, the telemetry link exhibiting the greatest signal strength, highest bandwidth or lowest noise level may be selected for the active telemetry link.

In one example, the time period for the loss of signal of the radio frequency synchronization state machine is programmable. In various examples, the time period is between 10 and 22,560 milliseconds. In one example, the time period for the loss of signal of the inductive synchronization state machine is programmable. In one example, the time period for the loss of signal of the inductive synchronization state machine is fixed. In one example, the fixed time period is 100 milliseconds.

In various examples, a loss of a signal provides the trigger to transition from one state machine to another. In one example, state machine selection is determined by an instruction provided by either implantable device 110 or external device 160.

In one example, more than one communication channel is active simultaneously. The data transmitted on the multiple communication channels, in various examples, is either the same or different. In one example, the data from multiple communication channels is reconciled by an arbitration algorithm or based on other factors such as noise level, bandwidth, reliability and signal quality. Other factors can be evaluated based on error detection/checking routines such as cyclic redundancy code checking or other protocol based mechanisms.

System 500 is illustrated using logical blocks, however, it is to be understood that portions, or all, of system 500 can be implemented in circuitry, logical gates or a processor executing a set of instructions stored in a memory. The set of instructions implements an algorithm for enabling data telemetry. In one example, system 500 is implemented using a firmware based state machine executing on a processor. In various examples, system 500 includes a controller coupled to each of the implantable transceiver circuits and provides circuitry or programming to selectively enable or disable data telemetry.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

What is claimed is:

1. An implantable device comprising:
   at least two telemetry circuits including a first telemetry circuit and a second telemetry circuit, each telemetry circuit configured to wirelessly communicate with an external device; and
   a controller coupled to each telemetry circuit, the controller configured to, after a communication session is established:
      operate a selected one of the first or second telemetry circuits in a synchronous state in which the telemetry circuit recurrently transmits data synchronized with a received synchronization signal associated with the selected telemetry circuit until the selected telemetry circuit detects loss of the synchronization signal; and
      operate the first and second telemetry circuits in an out-of-synchronization state, upon detection of the loss of the synchronization signal and before the communication session terminates, in which the implantable device monitors for both a synchronization signal associated with the first telemetry circuit and a synchronization signal associated with the second telemetry circuit and in which receipt of the synchronization signal associated with the first telemetry circuit causes the first telemetry circuit to transition to the synchronous state and in which receipt of the synchronization signal associated with the second telemetry circuit causes the second telemetry circuit to transition to the synchronous state,
   wherein the first telemetry circuit and second telemetry circuit are configured to recurrently transition to the out-of-synchronization state upon detecting loss of the associated synchronization signal before termination of the communication session.

2. The device of claim 1, wherein the controller is configured to operate the second telemetry circuit in the synchronous state after detecting a synchronization signal using the second telemetry circuit.

3. The device of claim 1, wherein the controller is configured to operate the first telemetry circuit in the synchronous state when a synchronization signal is detected by the first telemetry circuit when in the out-of-synchronization state.

4. The device of claim 1, wherein the second telemetry circuit is continuously powered.

5. The device of claim 1, wherein the first telemetry circuit and the second telemetry circuit are configured to simultaneously operate in the out-of-synchronization state.

6. The device of claim 1, wherein the first telemetry circuit and the second telemetry circuit are configured to sequentially operate in the out-of-synchronization state.

7. The device of claim 1, including a clock coupled to the controller to provide a signal after a predetermined period of time following a loss of the synchronization signal.

8. The device of claim 1, wherein the controller is configured to operate both the first telemetry circuit and the second telemetry circuit in the out-of-synchronization state upon detecting loss of the synchronization signal for a predetermined period of time.

9. The device of claim 8, wherein the predetermined period of time is remotely selectable.

10. The device of claim 1 wherein the controller is configured to select the first telemetry circuit and deselect the second telemetry circuit upon receiving an instruction from the external device.

11. The device of claim 1, wherein the first telemetry circuit includes at least one of a near field telemetry circuit and a far field telemetry circuit.

12. The device of claim 1, wherein the first telemetry circuit includes the near field telemetry circuit and includes an inductive antenna.

13. The device of claim 11, wherein the first telemetry circuit includes the far field telemetry circuit and includes a radio frequency antenna.

14. A method comprising:
monitoring for a synchronization signal from an external device using at least one of a plurality of wireless telemetry circuits of an implantable device, the plurality of telemetry circuits including a first telemetry circuit and a second telemetry circuit;
establishing a communication session using the implantable device;
operating a selected one of the first or second telemetry circuits in a synchronous state in which the telemetry circuit recurrently transmits data synchronized with a received synchronization signal associated with the selected telemetry circuit until the selected telemetry circuit detects loss of the synchronization signal; and
operating the first and second telemetry circuits in an out-of-synchronization state, upon detection of the loss of the synchronization signal and before the communication session terminates, in which the implantable device monitors for both a synchronization signal associated with the first telemetry circuit and a synchronization signal associated with the second telemetry circuit and in which receipt of a synchronization signal associated with the first telemetry circuit causes the first telemetry circuit to transition to the synchronous state and in which receipt of a synchronization signal associated with the second telemetry circuits causes the second telemetry circuit to transition to the synchronous state,
wherein the first telemetry circuit and second telemetry circuit are configured to recurrently transition to the out-of-synchronization state upon detecting loss of the associated synchronization signal before termination of the communication session.

15. The method of claim 14, wherein operating the first and second telemetry circuits in the out-of-synchronization state includes monitoring for the synchronization signal using the first telemetry circuit simultaneously with monitoring using the second telemetry circuit.

16. The method of claim 14, wherein operating the first telemetry circuit includes communicating using a near field telemetry circuit.

17. The method of claim 14, wherein operating the first telemetry circuit includes communicating using a far field telemetry circuit.

18. The method of claim 14, further including enabling data telemetry using the second telemetry circuit when the first telemetry circuit is not in the synchronous state.

19. The method of claim 14, further including selecting the first telemetry circuit for operation upon receiving a selection signal from a controller.

20. The method of claim 19, wherein receiving the selection signal includes receiving an instruction using at least one of the plurality of telemetry circuits.

21. A system comprising:
an external device having at least one external telemetry circuit configured to transmit a synchronization signal; and
an implantable device having at least two implantable telemetry circuits and a controller coupled to each of the at least two implantable telemetry circuits, the two implantable telemetry circuits including a first implantable telemetry circuit and including a second implantable telemetry circuit, the controller configured to, after a communication session is established:
operate a selected one of the first or second telemetry circuits in a synchronous state in which the telemetry circuit recurrently transmits data synchronized with a received synchronization signal associated with the selected telemetry circuit until the selected telemetry circuit detects loss of the synchronization signal; and
operate the first and second telemetry circuits in an out-of-synchronization state, upon detection of the loss of the synchronization signal and before the communication session terminates, in which the implantable device monitors for both a synchronization signal associated with the first telemetry circuit and a synchronization signal associated with the second telemetry circuit and in which receipt of a synchronization signal associated with the first telemetry circuit causes the first telemetry circuit to transition to the synchronous state and in which receipt of a synchronization signal associated with the second telemetry circuits causes the second telemetry circuit to transition to the synchronous state,
wherein the first implantable telemetry circuit and second implantable telemetry circuit are configured to recurrently transition to the out-of-synchronization state upon detecting loss of the associated synchronization signal before termination of the communication session.

22. The system of claim 21, wherein the controller is configured to simultaneously operate each implantable telemetry circuit in the out-of-synchronization state upon losing the synchronization signal for a predetermined period of time.

23. The system of claim 21, wherein the first implantable telemetry circuit includes a far field telemetry circuit.

24. The system of claim 21, wherein the controller is configured to enable a synchronous state using the first implantable telemetry circuit and configured to disable the synchronous state using the second implantable telemetry circuit upon receiving a synchronization signal using the first implantable telemetry circuit.

25. The system of claim 21, wherein the controller is configured to sequentially operate each of the at least two implantable telemetry circuits in the out-of-synchronization state.

* * * * *

UNITED STATES PATENT AND TRADEMARK OFFICE
CERTIFICATE OF CORRECTION

| | | |
|---|---|---|
| PATENT NO. | : 7,881,802 B2 | Page 1 of 1 |
| APPLICATION NO. | : 10/914499 | |
| DATED | : February 1, 2011 | |
| INVENTOR(S) | : Sylvia Quiles et al. | |

It is certified that error appears in the above-identified patent and that said Letters Patent is hereby corrected as shown below:

IN THE CLAIMS:

In column 13, line 1, in Claim 12, delete "claim 1," and insert -- claim 11, --, therefor.

Signed and Sealed this
Fifth Day of April, 2011

David J. Kappos
*Director of the United States Patent and Trademark Office*